US00PP15870P2

(12) United States Plant Patent
Saville

(10) Patent No.: US PP15,870 P2
(45) Date of Patent: Jul. 19, 2005

(54) MINIATURE ROSE PLANT NAMED 'SAVAPIZZAZZ'

(50) Latin Name: ***Rosa hybrida* minima**
Varietal Denomination: SAVapizzazz

(75) Inventor: John M. Saville, Newburyport, MA (US)

(73) Assignee: Nor'East , Miniature Roses, Arroyo Grande, CA (US)

( * ) Notice: Subject to any disclaimer, the term of this patent is extended or adjusted under 35 U.S.C. 154(b) by 0 days.

(21) Appl. No.: 10/837,016

(22) Filed: Apr. 30, 2004

(51) Int. Cl.[7] ..... A01H 5/00
(52) U.S. Cl. ..... Plt./116
(58) Field of Search ..... Plt./116

*Primary Examiner*—Anne Marie Grunberg
*Assistant Examiner*—Annette H Para

(57) ABSTRACT

'SAVapizzazz' is a new and distinct variety of miniature rose plant primarily identified by its long lasting flowers of brilliant red with a bright yellow reverse. The flower starts out a dark red and lightens down to near vermillion-red as the flower opens and the yellow reverse always looks bright. Its very glossy, dark green foliage has excellent disease resistance. The flower has good resistance to insects. The plant has an upright habit with flower stems suitable for cutting.

1 Drawing Sheet

Genus and species: *Rosa hybrida* 'minima'.
Varietal denomination: 'SAVapizzazz'.

CROSS REFERENCE

This new invention bears some resemblance to 'Poker Chip' (U.S. Plant Pat. No. 4,582, expired) and which is from this breeding program.

Similarities—Both roses are a vermillion-red with a bright yellow reverse, held upright on the plant; both plants primarily have 5 to 7 leaflet, glossy leaves; and good disease resistance.

Differences—This new invention is a little taller and has a more upright plant habit; the margins of leaflets of the new invention are uneven and doubly serrate; Poker Chip has even serration on the margins of its leaflets; leaflets are smaller on this new invention.

The relationship between these plants: the parentage of both varieties can be traced back to MORsheri (U.S. Plant Pat. No. 3,826, expired), the seed parent for 'Poker Chip' and the grandparent on the pollen side of 'MACpie' (not under patent protection), which is the pollen parent of the new invention. The pollen-parent for MACpie is Party Girl™ whose parentage is Rise n Shine (U.S. Plant Pat. No. 4,231) by MORsheri. Also, the pollen-parent of 'Rise n Shine' is 'Yellow Magic' (not under patent protection), and 'Yellow Magic' is the pollen-parent of the seedling listed as seed-parent for 'SAVasach'.

BACKGROUND OF THE INVENTION

This present invention relates to a new and distinct variety of hardy, bush type plant of the miniature rose class. This new variety originated in a greenhouse in Rowley, Mass. from a controlled crossing in 1991 of the following two rose plants:

The seed parent is 'SAVasach' (U.S. Plant Pat. No. 5,967).

The pollen parent is 'MACpie' (not under patent protection).

The main purpose of this breeding program is to produce unique miniature roses with hybrid tea form. We are trying to reintroduce fragrance into these roses along with disease resistance and hardiness. Our ideal miniature rose would have the two qualities of disease resistance and fragrance, along with hardiness and exhibition, hybrid tea form blooms in abundance from late spring to late fall.

Steps taken to achieve this goal: Various fragrant roses, not always of the miniature class, have been brought into this breeding program, which, besides fragrance, were chosen for disease resistance, hardiness, and hybrid tea, exhibition form. These fragrant roses are then crossed with minature roses, chosen for their disease resistance, hardiness and durability, quality of bloom production and preferably any degree of fragrance in hopes of producing fragrant, hardy, disease resistant, floriferous miniature roses.

How that relates to the new rose: The seed parent for this rose is a very fragrant, miniature rose, 'SAVasach', noted also for its abundant bloom production, good disease resistance and hardiness. The pollen parent, 'MACpie', is an exhibition form miniature rose of good disease resistance, hardiness, abundant bloom production and has a slight fragrance.

Similarities to its parents—This present invention bares resemblance to its parents in that they all have a degree of fragrance and good disease resistance. There are no other noticeable similarities to the seed parent.

The pollen parent is a miniature a very similar, upright, uniformly branched plant habit with glossy foliage and exhibition, hybrid tea form.

Differences from its seed parent—The color and size of bloom as well as plant habit. The seed parent is a lavender rose that rapidly opens near flat and has a more spreading plant habit. This new invention has blooms of vermillion red with a bright yellow reverse, that are slow to open and a very upright plant habit.

Obvious differences from its pollen parent—color and size of bloom. The pollen parent has pastel, orange-pink blend flowers opening to 2½ to 2¾ inches across; this current invention has vivid red flowers with a bright yellow reverse and blooms only opening to 1⅞ inches across.

Asexual reproduction by cuttings of this new variety in Rowley, Mass. and Arroyo Grande, Calif., shows that all distinguishing characteristics of this rose continually come true to form.

SUMMARY OF THE INVENTION

The present invention relates to a new and distinct variety of hardy dwarf bush type rose plant of the miniature class; the variety being primarily characterized by it's unique coloring of a brilliant, red with a bright yellow reverse. Among the features that distinguish this new variety from other similar cultivars of, which I am aware, are the particular shade of red with the bright yellow reverse, the proportion of red to yellow, especially on the inside surface of the of the petals and the minimal amount of blending between the two, and the bright and contrasting yellow appearing to completely cover the reverse of the petals.

The variety is further characterized by its glossy dark green foliage moderate fragrance its repeat blooming, late spring to mid fall has blooms borne usually singly on straight stems of good cutting length holds up well as a cut flower flowers that are extremely long lasting on the plant seasonally bears blooms suitable for exhibition.

exceptional disease resistance different color of the bloom and foliage as growing conditions decline from ideal. (As the growing media becomes more acid and nutrients become less available to the plant, the color of the flower lightens, most notably, the yellow, and the foliage takes on stronger anthocyanin coloring, especially in the older foliage. With the addition of lime and the necessary nutrition the plant recovers rather quickly and new flowers again have the deeper coloring)

A plant that grows and blooms both in the greenhouse and outdoors, providing decoration in the garden or border and in large.

BRIEF DESCRIPTION OF THE DRAWING

The accompanying color photograph taken in April shows individual specimens of this new variety, 'SAVapizzazz' of the buds and flowers in different stages of development, and young and older leaves and stems as grown under plastic in San Luis Obispo County, Calif.

BOTANICAL DESCRIPTION OF THE PLANT

Following is a detailed description in outline form pertaining specifically to this new and distinct variety of miniature rose plant. All major color plate identifications made are referring to The Royal Horticulture Society Chart except where common terms of color definition are employed.

Genus/species: *Rosa hybrida* minima.

Commercial class: Miniature Rose.

Varietal denomination: SAVapizzazz.

The following is a description, in outline form, of SAVapizzazz as observed in April from specimens of 6 or more years of age, that had been grown indoors, under plastic in a 4-gallon container in Essex County, Mass., and less than one year old, grown in San Luis Obispo County, Calif. The later supplied statistics for new and young growth and flowers.

Blooming habit: Repeat bloomer.

Born: Singly.

Bud:

*Size.*—9/16 to 10/16 of an inch in length and 7/16 to 8/16 inch diameter at the widest point just before the sepals divide.

*Form.*—Ovate with an acute tip and a truncate base; as it first opens, it is urceolate.

*Color.*—When sepals first divide—between 8C and 8D.

Sepals:

*Color.*—Outer surface (anthocyanin coloration present only at the tips where they extend beyond the tip of the bud). Inside surface—tomentose, giving the appearance of being near 138C with a central, small pyramidal area from the base of the sepal to about 2/3 of the way up appearing near 145C. Outside surface; a light yellow-green, near 144 C near the base, near 144A along the margins and the portion in between which makes up the majority of the surface, is near 144B.

*Characteristics.*—Lanceolate; extending 7/16 to 8/16 inch beyond the tip of the bud just before the sepals start to divide; the general shape is elliptical with a truncate base; all tips terminate with a gland; other descriptions of the tips are described below the outside surface of the 2 innermost sepals has a minimal number of hairs with a few more toward the tips and an even greater amount on the tips that extend beyond the tip of the bud; the margins are entire and lined with hairs and a smattering of glands and/or stipate glands; there sizes are different on the same bud, 19/32 to 21/32 inch long plus the sharply acuminate tips are an additional 6/32 to 9/32 inch, and 7/32 to 9/32 inch wide.

The 2 outside surface of the outermost sepals have a minimal number of hairs; the margins are lined with hairs and a smattering of glands and/or stipate glands; there are 2 or 3 foliar, lanceolate appendages on each margin and 1 or 2 more along the margins of the tip; the margins of the tips and the foliar appendages are void of hairs but do have 0 to 3 glands, usually having 1 or 2; the length of the outer sepals averages 21/32 inch long plus the lanceolate tips are an additional 10/32 to 12/32 inch, and they are 7/32 to 9/32 inch wide excluding the flags.

The one sepal in between the inner and outer sepals is a combination of the others, having one margin entire and the other usually with 2 foliar lanceolate appendages and a lanceolate tip; 19/32 to 20/32 in length plus the sharply acuminate tip is an additional 9/32 to 11/32 inch, and 9/32 inch wide excluding the flags; the only margins void of hairs are the foliar appendages.

The sepals start rolling back with the petals but then roll quickly all the way back till the tips touch the stem; permanently attached to the receptacle which usually dries and eventually drops from the plant; occasionally a hip will form with the sepals remaining permanently attached to the top of the hip, still rolled all the way back so they are resting on the top of the hip.

Peduncle: Averaging ½ inch in length and 3/32 to 4/32 inch in diameter.

*Aspect.*—Straight.

*Strength.*—Strong.
*Color.*—(Anthocyanin coloration absent) near 144B.
*Appearance.*—Glossy.
*Texture.*—Glabrous.

Receptacle: Diameter—9/32 to 10/32 inch.
*Color.*—Near 144C.
*Appearance.*—Glossy.
*Texture.*—Glabrous.

Bloom:
*Size.*—When fully expanded — about 1⅞ inches across and a depth of 15/32 inch.
*Form.*—The upper profile opens flat and remains flat for the duration; the lower profile remains cupped only expanding in width; the reflex of the petals is slight from flower opening to petals drop.
*Petalage.*—Under normal conditions, 17 to 18 on young plants and up to 28 on mature plants (3 years or older).
*Petaloids.*—Usually 4 to 5.
*Fragrance.*—Mild.
*Lasting quality as cut flower.*—10 to 14 days.

Petals:
*Texture.*—Smooth; glabrous.
*Appearance.*—Inside velvety and outside satiny.
*Form.*—Widely obtuse.
*Apex.*—Rounded.
*Margin.*—The upper margin being emarginated, retuse or up to 5 serratures along the upper margin or a combination of notches and serratures on the outermost petals causing them to appear ruffled; inner and middle petals have 1 to 4 notches and/or serratures, most often a central serrate at the apex and a single notch on either side, but also occasionally being emarginate.
*Base of the petals.*—Is usually oblique (broadly oblique might best describe it) causing the entire petal to appear lopsided until halfway up the outer margin where it evens off.
*Length and width.*—Outer petals are 14/16 to 15/16 inch wide by 13/16 inch long.
*Arrangement.*—Imbricated.
*Persistence.*—Usually drop off cleanly in 24 to 28 days.
*Color is the same for inner and outer petals, throughout the life of the bloom.*—As the bloom first opens the inner surface is near 46A, from the red group, from the margins downward to the last ¼ inch where it lightens slightly as it blends in with the coloring at the base of the petals which is the lower 3/16 inch, where the color is a bright yellow between 7B and 7C down to the point of attachment; rarely there is a streak up the center of the 1 or 2 of the outer petals which is white, near 155C, which may feather out near the top of the petal. Reverse is near 46A just along the outer margin, which suffuses downward through the near 8B into the near 8A near the base and at the point of attachment, the reverse frequently has some veins, always includes the main vein, which may be near 149B starting at the point of attachment and going ⅔ or less of the way up the petal; the reverse of any petals that have a white streak on their top surface, have a streak up the back that is the same color as that of the base. When half blown, the inner surface is between 46B and 42A, a more orange-red, from the margins downward and the yellow at the base is between 9C and 6C.
*At point of attachment.*—Is a bit brighter yellow, near 7C.
*Reverse.*—Also slightly lighter, the yellow is near 10C near 10B near the base.
*At point of attachment.*—Near 10A. As the bloom ages it continues to lighten to the primary part of the upper surface being near 32A, then to between 32A and 30A and in its last days, just before the petals drops, the red picks up a slight bluing, becoming near 53C on the upper surface and generally near 8D and near 10D at attachment; the near 10C for the upper portion of the petal near 6C near at the base.
*General tonality after a few days.*—Vermillion red with bright yellow reverse.
*General tonality from a distance.*—Bright red with a bright yellow reverse.

Petaloids:
*Colors.*—Same as outer petals.
*Texture.*—Smooth, velvety.
*Size.*—Width — 3/16 to 4/16 inch at the widest point and 7/16 to 8/16 inch long.
*Unique characteristics.*—Usually half a petal, length wise, usually includes the mid-vein which is near 8B unless they are epipetalous, causing that edge to be the color of the filaments or stamens or in combination with the 8B of the mid vein.

REPRODUCTIVE ORGANS

Stamens, filaments and anthers:
*Arrangement.*—(Regularly arranged around styles).
*Quantity.*—Between 97 and 103.
*Filaments.*—Length — between 2/16 and 3/16 inch. Color—a light yellow-green, near 154D.
*Anthers.*—Color—near 163D from the greyed-orange group.

Pollen:
*Color.*—Near 163C from the greyed-orange group.
*Quantity.*—Small amount.

Pistils, styles and stigmas:
*Quantity.*—About ⅓ as many as the stamens.
*Styles.*—Straight, thin, near even in length.
*Length.*—Near ⅛ inch long with the outermost row being only 3/32 inch long. Color—a very light yellow, near 4D.
*Stigmas.*—Color—near 163C from the greyed-orange group.

Hips:
*Shape.*—Rounded, pumpkin shaped with both the bottom and top being truncate.
*Size.*—Average 7/16 inch diameter and 13/32 inch deep measuring from where it was connected to the pedicel, upward, to the top.
*Surface texture.*—A few randomly placed hairs.
*Surface appearance.*—Glossy.
*Color when mature.*—A small portion usually is near 163B; a larger is often near 169B and the side most towards the sun is deep red-orange, closest to a mix of near 185A and 169A.
*Seeds.*—Occasionally one seed will partially protrude from the top, usually having 3 seeds per hip. Color—mature seed coat is between 166B and 172B of the greyed-orange group. Shape—usually 5 sided, near flat on one side, each side is individually rounded but seed is not round. Size—between 3/16 and 4/16 inch top to bottom and a diameter near 7/32 inch.

PLANT

Habit: Upright uniformly branched.

Growth: Average vigor, 16 to 24 inches tall and 15 inches wide (can get up to 24 inches wide in warm climates where there is no winterkill).

Diameter of stems: Main stalk is between 11/32 and 13/32 inch. Primary laterals are between 13/64 and 14/64 inch and secondary laterals have a diameter of 11/64 inch.

Length of flowering stem: On occasion, as much as 16.5 inches or as short as 4.5 inches, the most common length being between 10 and 11 inches.

Foliage: Pinnately compound with 5 to 7 leaflets, occasionally with 3 leaflets.

*Quantity.*—3 or 4 leaves per 2 inches of stem length; the number of 7 leaflet leaves is random, there may be none or there may be as many as 3 in the 2 inches of stem length.

*Distance between nodes.*—Usually 6/8 to 7/8 inch.

*Length of mature leaf.*—As much as 3 9/16 inches or as short as 2 15/16 inches when measured along the petiole/rachis from the plant stem to tip of terminal leaflet. Mean length is about 3 2/16 inches.

*Leaflets.*—The basal leaflets are often frequently not attached directly opposite each other, being off by up to much as 1/8 inch. Leaflet shape is ovate with an acute tip and the base is usually obtuse but occasionally oblique. The widest point of mature terminal leaflet is between 12/16 and 13/16 inch. Length of mature terminal leaflet is about 1 1/8 inches inch from point of its attachment to the petiolule to its apex. First pair of leaflets below the terminal leaflet are usually not the same size, one being 1/64 to 1/8 inch wider and longer than its counterpart, both averaging 4/8 to 5/8 inch wide and 13/16 to 1 1/16 inch long. Color new foliage, anthocyanin coloration strong: upper surface, near 137A flushed with near 59A under surface, near 138A, with all or only random portions flushed with near 178A older foliage—anthocyanin coloring absent upper surface is near 137B under surface is near 138B glands along the margin are near 178A and sometimes the color is noticeable to the naked eye, giving the appearance that the leaf margin itself is near 178A. Appearance—Upper surface, glossy underside, matte with veins protruding; primary veins protrude quite noticeably and are flushed with near 178A until the foliage is over 6 weeks old, when the anthocyanin coloring seems to disappear; lateral veins protrude very slightly and are only occasionally flushed with the anthocyanin coloring after the first 3 weeks.

*Texture.*—Upper surface of the terminal leaflet is glabrous; upper surface of the remainder of the leaflets is nearly glabrous, having from 1 to 4 hairs and at least one of those hairs is somewhere on the primary vein under surface—leathery and glabrous.

*Leaflet margin.*—Uneven serration and doubly serrate with glands at the tip of each serrate and rarely in-between the serratures.

*Petiole.*—Color on young leaf—upper side is entirely near 187A for the first couple of weeks, then becoming near 145C at the base, suffused with 187A, up as far as the stipules are attached underside is near 144B suffused with near 178A the anthocyanin coloring disappears gradually as the leaf ages and is usually gone from the lower portion of the petiole where the stipule are attached after 3 weeks and not completely gone from the upper portion of the petiole until after 6 weeks. Color on old leaf, upper side—near 147C in the groove and near 147A along the ridge; underside near 146C. Texture—upper side 3 to 4 hairs per 1/4 inch in the groove and numerous stipate glands along the ridge; twice as many hairs are found in the groove just below the basil leaflets; the point where the stipate glands angle outward is the point where the first hairs appear. underside—glabrous petiole length is 11/16 to 1 1/16 inch long petiole width and depth are from 3/64 and 4/64 inch.

*Rachis.*—Color on young leaf—Upper side is entirely near 187A underside is near 178A color on old leaf, upper side: near 147C in the groove and near 147A along the ridge; underside near 146B.

*Texture.*—Upper side, 1 to 2 hairs and 0 to 2 stipate glands per 1/4 inch; there are 3 or 4 stipate glands just below the point where the petiolules are connected and numerous hairs at the point where the petiolules are connected underside—glabrous rachis length 7/8 inch on 5 leaflet leaves and averaging 31/32 inch on 7 leaflet leaves; width and depth are from 2/64 and 3/64 inch.

*Petiolules.*—Color on young leaf, upper side, is the same as that of the ridge of the rachis at the point where they are attached underside coloring is the same as that of the underside of the rachis where they are attached. Color on old leaf—146C in the groove and near 144A along the ridge underside is near 144D. Petiolule length is usually 3/64 but may be as long as 5/64 inch; on 7 a leaflet leaf the basil leaflets are 2/64 to 3/64 inch in length; diameter is 3/64 to 4/64 inch. Texture—Upper surface—0 to 1 hair in the groove and 0 to 2 stipate glands on the ridges; under surface—0 to 1 hair.

*Stipules at petiole base.*—Near 1/16 inch wide or less, slightly arcuate, occasionally appearing non-existent until they angle out from the stem. Margins loosely roll under and are loosely serrate with stipate glands at the tip of and In-between each serrate; when the stipules appear non-existent, the margins are nearly entire but having glands and stipate glands along the margin on mature leaf, attached to each side of the petiole for 3/8 to 4/8 inch and then turning outward at a 55 to 85° angle for another 1/8 to 2/8 inch, and one side being shorter than the other by 1/64 inch; the upper surface of the portion that angles out has stipate glands along the margins as well as a few hairs just at the tips; under surface is glabrous. Color of the stipules is the same as the leaflets.

Resistance: Excellent resistance to downy and powdery mildews and blackspot; very good resistance to insects; no rust observed.

Wood:

*New wood.*—Texture—smooth.

*Appearance.*—There are a few nearly imperceptible hairs, not visible to the unaided eye on each 0.5 inch of stem and on growth over 3 months old there is also a stipate gland. Color on new growth is near 145A flushed with near 178B; young wood is near 143C and then becoming near 137B.

*Old wood.*—The oldest wood being 5 or more years old is a shade of brown, nearest 177B; stems that are 3 to 4 years old are a medium green, some near 148A and some between 147A and 148A, both with corky patches of a lighter brown, near 177D.

Lenticels: On wood that is 4 years or older there are 4 to 6 lenticels per half-inch of stem on the surface facing away from the center of the plant; the 3 remaining sides of the stems have between 3 and none per half-square inch of stem surface—this apparently is not related to exposure to sunlight. Lenticels start appearing on the stem within their first 6 months where you might find 1 on 2 to 4 inches of stem, in their 3rd year there can be 1 or 2 per half-inch of stem length.

Prickles:

*Quantity on main stalks.*—Usually 4 to 6 per inch of stem, 1 or 2 averaging 7/32 inch long and the remainder being very small, between 2/32 and 3/32 inch long.

*On laterals.*—May be as many as 27 very small prickles, 1/32 to 3/32 inch long, per inch of stem and 1 or 2 being 7/32 to 8/32 inch long; the greatest quantity of the very small prickles is near the nodes and lower down on the plant, apparently losing many of these small prickles as the plant grows, always holding onto the 1 or 2 larger ones.

*Size and form.*—The base of the prickles is narrow elliptical and attached to the stem for a distance equal to its length; the prickles are angled slightly downward, tapering quickly to a point.

*Color.*—On new growth is near 59C, when young, becoming near 178C when old—near 165A and on the oldest canes, near 197B. There are no prickles on the underside of the petiole or rachis.

Hardiness: Tested hardy in zones 5 through 9 with winter protection recommended for zones and colder; tested in Horticultural Society heat zones 7 trough 4.

It is claimed:

1. A hardy, new and distinct variety of rose plant of the miniature class is claimed, substantially as herein illustrated and described, with billiant red flowers having a bright yellow reverse, mild fragrance, and few thorns on an upright growing plant with dark green, glossy foliage and having very good disease resistance.

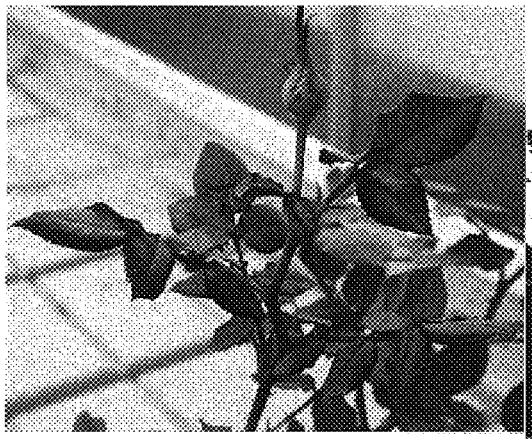
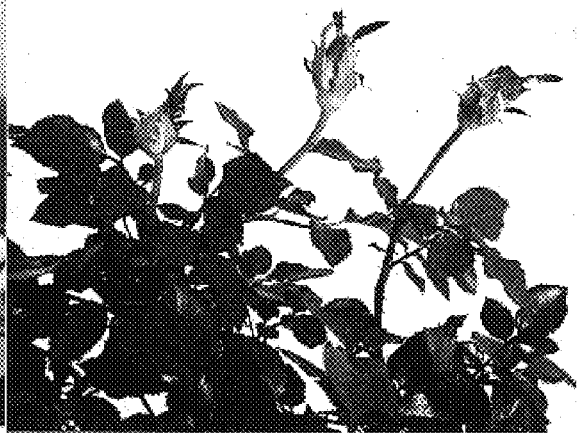
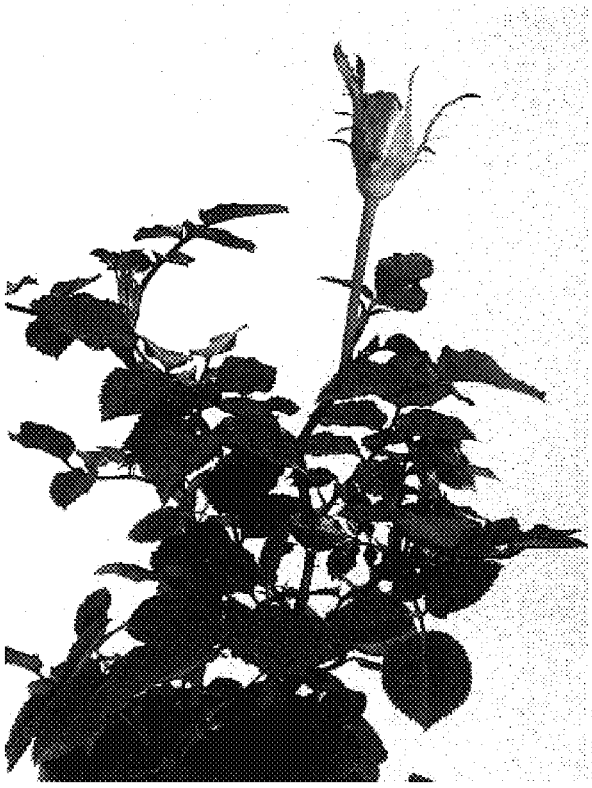
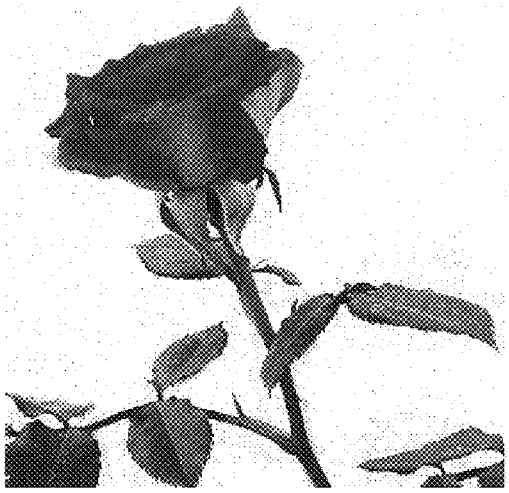
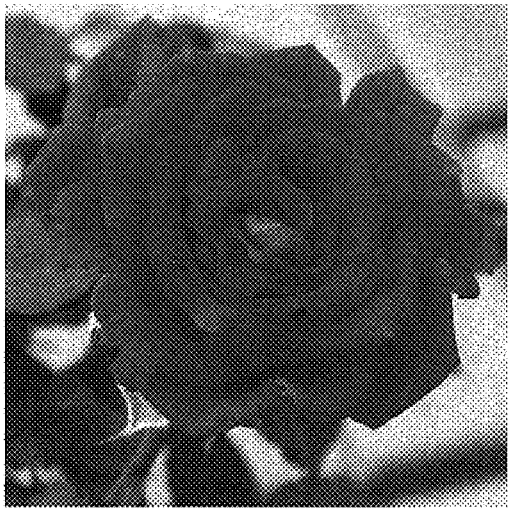

* * * * *